United States Patent [19]

Matsumoto et al.

[11] Patent Number: 5,017,697

[45] Date of Patent: * May 21, 1991

[54] PROCESS FOR PURIFYING SUCROSE FATTY ACID ESTERS HAVING HIGH HLB

[75] Inventors: Shusaku Matsumoto, Kyoto; Yoshio Hatakawa, Higashiosaka; Akihiko Nakajima, Kyoto, all of Japan

[73] Assignee: Dai Ichi Kogyo Seiyaku Co., Ltd., Kyoto, Japan

[ * ] Notice: The portion of the term of this patent subsequent to Feb. 26, 2008 has been disclaimed.

[21] Appl. No.: 373,014

[22] Filed: Jun. 28, 1989

[30] Foreign Application Priority Data

Jun. 29, 1988 [JP] Japan .................. 63-162267

[51] Int. Cl.$^5$ .................. C07H 1/00; C07H 13/00; C08B 37/00; C13D 1/00
[52] U.S. Cl. .................. 536/127; 536/115; 536/119; 536/120; 536/124
[58] Field of Search .............. 536/127, 124, 119, 115, 536/120

[56] References Cited

U.S. PATENT DOCUMENTS

| | | | |
|---|---|---|---|
| 3,748,324 | 7/1973 | Mizutani et al. ............ | 536/119 |
| 3,792,041 | 2/1974 | Yamagishi et al. .......... | 536/119 |
| 4,252,834 | 2/1981 | Inamine et al. ............ | 426/103 |

FOREIGN PATENT DOCUMENTS

| | | |
|---|---|---|
| 42-8850 | 4/1942 | Japan . |
| 42-11568 | 6/1942 | Japan . |
| 48-10448 | 4/1973 | Japan . |
| 809815 | 3/1950 | United Kingdom . |
| 958064 | 5/1964 | United Kingdom . |

OTHER PUBLICATIONS

Abstract of Japanese Patent Publication No. 8850/67, Derwent Japanese Patents Report, vol. 6, No. 16, 1967, General Organic-p. 4.
Abstract of Japanese Patent Publication No. 11568/67, Derwent Japanese Patents Report, vol. 6, No. 26, Aug. 22, 1967, General Organic-p. 1.

Primary Examiner—Ronald W. Griffin
Assistant Examiner—Everett White
Attorney, Agent, or Firm—Armstrong, Nikaido, Marmelstein, Kubovcik & Murray

[57] ABSTRACT

A process for recovering, in a purified form, sucrose fatty acid esters having a high HLB included in a reaction mixture formed by a reaction of sucrose and a fatty acid alkyl ester in an organic solvent as reaction medium in the presence of a catalyst, which comprises adjusting the reaction mixture from which a part of the organic solvent may be previously removed and to which water is added to form an aqueous solution, to a neutral pH region, adding a neutral salt and sucrose to the solution to precipitate the sucrose fatty acid esters, separating and washing the precipitate with an acidic water, and subjecting the washing liquid to ultrafiltration. The concentrate obtained by ultrafiltration may be spray-dried to form a dry powder of the sucrose esters having high HLB, and the liquid obtained by separating the precipitate may be contacted with a reverse osmosis membrane to recover sucrose. According to the invention, purified sucrose fatty acid esters having high HLB can be obtained from the reaction mixture without using an organic solvent as purification solvent, while sucrose can be recovered in high yield.

25 Claims, 2 Drawing Sheets

WATER(%) + TOTAL SALT(%) + TOTAL SUCROSE(%) = 100(%)

WATER(%) + TOTAL SALT(%) + TOTAL SUCROSE(%) = 100(%)

MONOESTER + DIESTER + TRIESTER = 100%

PROCESS FOR PURIFYING SUCROSE FATTY ACID ESTERS HAVING HIGH HLB

BACKGROUND OF THE INVENTION

The present invention relates to the recovery of sucrose fatty acid esters having a high HLB (hydrophilic-lipophilic balance) from the reaction mixture containing them. More particularly, the present invention relates to an industrially useful process for purifying sucrose fatty acid esters having a high HLB included in the reaction mixture formed by a reaction of sucrose and fatty acid alkyl esters in an organic solvent medium, while recovering the unreacted sucrose in high yield.

Sucrose fatty acid esters (sugar esters) useful as surface active agents are prepared industrially at present by either a solvent process wherein sucrose is reacted with a methyl ester of a higher fatty acid having 8 to 22 carbon atoms in the presence of a suitable catalyst in an organic solvent such as dimethylformamide or dimethylsulfoxide, as disclosed in Japanese Patent Publication Kokoku No. 35-13102; or an aqueous medium process wherein sucrose is formed into a molten mixture with a fatty acid salt (soap) using water without using an organic solvent, and is then reacted with a higher fatty acid methyl ester in the presence of a catalyst, as disclosed in Japanese Patent Publication Kokoku No. 51-14485.

However, even according to any of these processes, the obtained reaction mixture contains impurities such as the unreacted sucrose, the unreacted fatty acid methyl ester, residual catalyst, soap, free fatty acid, volatile material (reaction solvent), etc. in addition to the desired sucrose fatty acid ester. These impurities, at least impurities whose contents exceed the specified amounts must be removed prior to being put on the market. Particularly, in case of sucrose fatty acid esters used as a food additive which requires a high purity, removal of the solvent (volatile material) remaining in the product is very important in view of strict regulation, e.g. provision by FDA, U.S.A. according to which allowable content of remaining dimethylsulfoxide in sucrose fatty acid esters is at most 2 p.p.m. [Fed Regist., 51(214), 40160-1].

In general, the conversion of sucrose is low. For example, in case of the process using dimethylformamide as the reaction medium, the conversion is at most 50 %. Accordingly, recovery of the unreacted sucrose is also important.

In order to remove the remaining organic solvents and to recover the unreacted sucrose from the reaction mixture (namely crude sucrose fatty acid esters), various processes for the purification of crude product have hitherto been proposed These purification processes usually require a large amount of organic solvents (for example, butanol, toluene, methyl ethyl ketone as disclosed in Japanese Patent Publication Tokkyo Kokoku No. 42-11588 and No. 48-10448). However, in the production of sucrose fatty acid esters on an industrial scale, the use of a large amount of organic solvents has the following disadvantages: (1) risk of explosion and fire, (2) provision of explosion and fire prevention means to electric devices, (3) application of closed system to production equipment for explosion and fire prevention, (4) requirement of fireproof construction for entire building by way of precaution against explosion and fire, (5) rise in fixed cost due to the items (2), (3) and (4), (6) rise in materials cost due to loss of solvent, (7) contamination of the product with remaining solvent, and (8) adverse influence on health of workers, and increase of cost resulting from increase in labor required for the prevention therefor.

In view of these circumstances, it has been desired to develop a purification technique capable of removing the unreacted sucrose and other impurities from the crude reaction mixture without using organic solvents.

Thus, purification processes using no organic solvent have hitherto been proposed For example, as representative methods, there have been known (1) a method wherein a sucrose fatty acid ester is precipitated by addition of an acidic aqueous solution to the reaction mixture, as disclosed in British Patent No. 809,815 and (2) a method wherein a sucrose fatty acid ester is precipitated by addition of an aqueous solution of a common neutral salt to the reaction mixture, as disclosed in Japanese Patent Publication Tokkyo Kokoku No. 42-8850.

However, these methods have disadvantages. When an acidic aqueous solution, for example, hydrochloric acid, is added to the reaction mixture as in the method (1), the sucrose fatty acid ester immediately deposits, but the unreacted sucrose is easily decomposed and converted into glucose and fruit sugar. This cannot be avoided even if the addition is conducted at a low temperature (e.g. 0° to 5° C). Accordingly, the recovery and reuse of the unreacted sucrose are difficult.

The addition of an aqueous solution of a neutral salt such as sodium chloride or Glauber's salt, as in the method (2), causes sucrose fatty acid esters to deposit rapidly. In this case, decomposition of unreacted sucrose does not occur, but the monoester which is an effective component in the product is dissolved in an aqueous phase. Consequently, not only the dissolution results in a large loss of the product, but also it is a hindrance particularly to production of sucrose fatty acid esters having a high HLB which are recently in great demand. Usually, the sucrose esters have an HLB value of 1 to 20, and the larger the HLB value, the higher the hydrophilic property.

Also, in Japanese Patent Publication Tokkyo Kokai No. 51-29417, it is proposed to utilize a property that a mixture of water and a solvent used for purification (hereinafter referred to as "purification solvent") separates into an upper light layer and a lower heavy layer Generally, the lower layer contains a large amount of water and, therefore, the unreacted sucrose, which is hydrophilic, and a salt derived from a catalyst used in the synthesis of sucrose fatty acid esters are dissolved in the lower layer Since the upper layer contains the purification solvent in a large quantity, compounds having a small polarity such as sucrose fatty acid esters, fatty acids and unreacted fatty acid methyl esters are dissolved in the upper layer. On the other hand, the solvent used for the reaction such as dimethylsulfoxide is dissolved not only in the lower layer, but also inconveniently in the upper layer. Consequently, it is impossible to completely separate the reaction solvent only by this method. The product is contaminated with a trace amount of the reaction solvent, and the removal of such a trace amount of the solvent requires a further large amount of purification solvent.

In order to industrially realize the purification of crude sucrose fatty acid esters using water, it is very important that the reaction solvent and the purification solvent are completely removed and moreover sucrose and the product are not lost.

Another important problems which must also be taken into consideration are recovery of the unreacted sucrose and drying of wet product, incident to the use of water as a purification solvent.

Since the purification of the reaction mixture with the use of water is based on difference in water solubility between a sucrose fatty acid ester and unreacted sucrose, migration of a large amount of unreacted sucrose into an aqueous phase cannot be avoided. The manufacture of sucrose fatty acid esters cannot be industrially accepted unless such a dissolved sucrose is recovered. Accordingly, it is very important to efficiently recover the sucrose which has transferred into an aqueous phase upon purification.

The water-containing sucrose fatty acid ester which has been separated from the reaction mixture and to be dried, is usually in the form of an aqueous solution when the water content is over 80 % by weight, and is in the form of a slurry when the water content is less than 80 % by weight. In general, an aqueous solution of a sucrose fatty acid ester shows a peculiar viscosity behavior such that the viscosity rapidly increases from about 40° C., reaches maximum at about 50° C. and rapidly drops over 50° C. Some problems are encountered in removing water from the sucrose fatty acid ester in the form of an aqueous solution or slurry. The evaporation of water by heating under vaccum, for example, using a usual agitated vacuum dryer, is practically difficult because of marked foaming. Moreover, when the evaporation is conducted at a high temperature and the contacting time with a heating source is long, not only the sucrose fatty acid ester is decomposed, resulting in marked coloration or caramel formation, but also the acid value is raised by free fatty acid formed by decomposition, as disclosed in Japanese Patent Publication Tokkyo Kokoku No. 37-9966. In particular, due to the property of sucrose fatty acid ester that the softing point or melting point is low (for example, sucrose monostearate having a melting point of about 52° C., and sucrose distearate having a melting point of about 110° C.), the sucrose fatty acid ester itself tends to be hydrated at the final stage of evaporation of water. This makes the dehydration more difficult. In addition, it is also a cause which make the drying difficult that the latent heat of evaporation of water is very high (more than 500 kcal/kg H2O) and the evaporation temperature is high.

Other usual drying methods are also not suitable for preparing dry sucrose fatty acid esters. For example, in case of using a flash dryer wherein a slurry is continuously heated, fed to a vacuum chamber and released thereto, various difficulties are encountered when a sufficient drying is desired because of a large latent heat of water. Even if these difficulties are overcome, the sucrose ester dehydrated and dried under vaccum is in the molten state and, therefore, it requires a pulverization step after taking out of the drier and cooling to less than the melting point to solidify, for instance, by blowing a cold air. In addition to many steps being required, there is a risk of dust explosion in the final pulverization step.

Accordingly, it is also important to solve the problems encounted by drying in realizing the purification of sucrose fatty acid esters using water as the purification solvent.

It is a primary object of the present invention to provide a process for recovering a purified sucrose fatty acid ester having a high HLB from the reaction mixture without using organic solvents as the purification solvent.

A further object of the invention is to provide a process for recovering a sucrose fatty acid ester free from organic solvents from the crude reaction mixture, with recovery of unreacted sucrose in high yield.

A still further object of the invention is to provide an industrially useful process for purifying a sucrose fatty acid ester using water as the purification solvent without substantial loss of the sucrose fatty acid ester and sucrose.

Another object of the invention is to provide a process for preparing a dry powder of a highly pure sucrose fatty acid ester having a high HLB with ease and without deteriorating the quality in the drying step, while recovering the unreacted sucrose.

These and other objects of the present invention will become apparent from the description hereinafter.

SUMMARY OF THE INVENTION

The present inventors have made experiments about salting out in the purification of crude product using water as the purification medium in order to achieve the following purposes namely (1) minimizing the amount of sucrose fatty acid esters dissolved in an aqueous phase, and if possible, decreasing it up to zero so as to precipitate the whole of sucrose fatty acid esters, (2) preventing decomposition of unreacted sucrose, (3) separating the reaction solvent from the sucrose fatty acid esters by dissolving the remaining reaction solvent in the aqueous phase, (4) purifying the precipitated sucrose fatty acid esters and forming a dry powder thereof, and (5) efficiently recovering the unreacted sucrose from the filtrate (or supernatant) obtained by removing the above-mentioned precipitate.

It has been found that when sucrose and a neutral salt are dissolved in an aqueous solution of the reaction mixture, the whole of the sucrose fatty acid esters is precipitated under a proper combination of pH, temperature, concentrations of neutral salt and sucrose, and amount of water, and moreover, surprisingly, the reaction solvent and a salt derived from the reaction catalyst are dissolved in the aqueous phase with the unreacted sucrose. Thus, on the basis of this dicsovery, it has now been found that the remaining volatile material (remaining reaction solvent) can be transferred completely into the aqueous phase, without substantial loss of sucrose fatty acid esters, by repeating the salting out procedure, namely by dissolving the precipitated sucrose fatty acid esters again in water and repeating the precipitation procedure by the addition of an aqueous solution of the neutral salt and sucrose, and that the unreacted sucrose can be efficiently recovered from the residual liquid after removal of the above precipitate by contacting it with an adequate reverse osmosis membrane.

It has been further found that sucrose fatty acid esters having a high HLB included in the precipitate is transferred into an aqueous phase with soluble impurities by washing the precipitate with an acidic water having an appropriate pH, while leaving sucrose fatty acid esters having a low HLB as the solid, and that the recovery of sucrose fatty acid esters having a high HLB transferred into the aqueous phase, which has not been achieved by conventional processes, can be made on an industrial scale by means of ultrafiltration to give an aqueous solution of purified sucrose esters and from which a powder can be obtained without deterioration of the quality by spray drying.

In one of the aspects of the present invention, there is provided a process for purifying sucrose fatty acid esters having a high HLB included in a reaction mixture formed by a reaction of sucrose and a fatty acid alkyl ester in an organic solvent, said reaction mixture containing sucrose fatty acid esters, unreacted sucrose, unreacted fatty acid alkyl ester, a reaction catalyst, a soap, a fatty acid and the organic solvent, which comprises adjusting the reaction mixture to a neutral pH region, adding water, a neutral salt and sucrose to the reaction mixture to precipitate the sucrose fatty acid esters, separating the resulting precipitate, washing the precipitate with an acidic water, neutralizing the washing liquid and subjecting it to ultrafiltration.

In another aspect of the present invention, there is provided a process for preparing a powder of sucrose fatty acid esters having a high HLB from a reaction mixture formed by a reaction of sucrose and a fatty acid alkyl ester in an organic solvent, said reaction mixture containing sucrose fatty acid esters, unreacted sucrose, unreacted fatty acid alkyl ester, a reaction catalyst, a soap, a fatty acid and the organic solvent, which comprises adjusting the reaction mixture to a neutral pH region, adding water, a neutral salt and sucrose to the reaction mixture to precipitate the sucrose fatty acid esters, separating the resulting precipitate from the aqueous phase, washing the precipitate with an acidic water, neutralizing the washing liquid and subjecting it to ultrafiltration, and spray-drying the resulting concentrate.

In still another aspect, from the aqueous phase obtained by separation of the precipitate after salting out, sucrose is recovered by subjecting the aqueous phase to reverse osmosis.

Thus, according to the present invention, from the reaction mixture, it is now possible (1) to remove the impurities, (2) to recover unreacted sucrose, (3) to obtain a powder of purified sucrose fatty acid esters having a high HLB and (4) to separate SE product into sucrose fatty acid esters having a high HLB and those having a low HLB, without using organic solvents on an industrial scale.

BRIEF DESCRIPTION OF THIS DRAWINGS

FIG. 1 is a triangular graph showing the relationship between the amount of each of water, total sucrose and total salt, and the amount of sucrose fatty acid ester dissolved in aqueous phase; and FIG. 2 is a triangular graph showing the relationship between the substitution degree of sucrose fatty acid esters and the cake-liquid equilibrium in acidic water.

DETAILED DESCRIPTION

Figure 1:
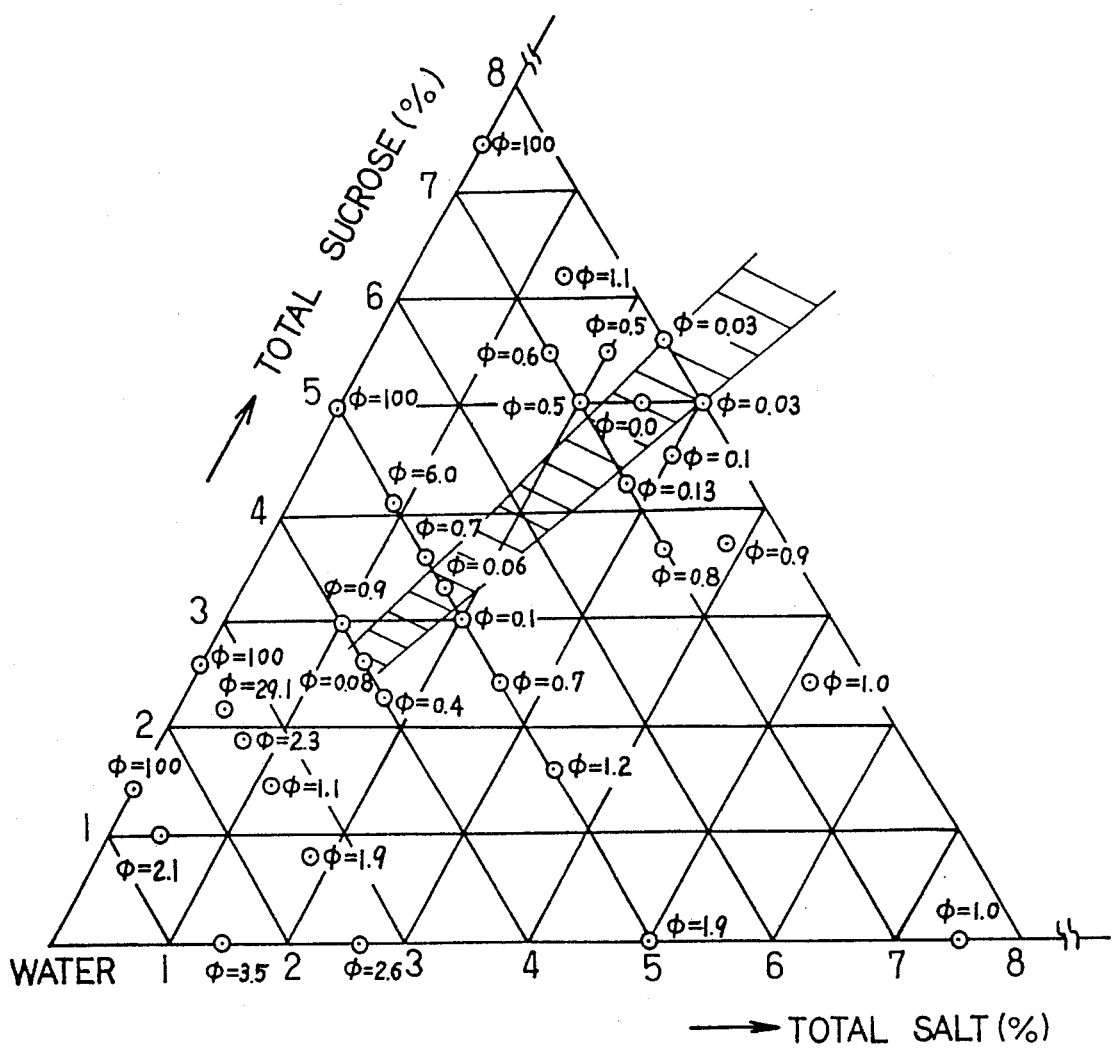

The process of the present invention is applicable to reaction mixtures obtained in the synthesis of sucrose fatty acid esters (hereinafter referred to as "SE") by a known reaction using an organic solvent as reaction solvent.

In the synthesis of SE using an organic solvent as reaction medium, generally the solvent, for example, dimethylsulfoxide is added to a mixture of sucrose and a fatty acid methyl ester in an amount of several times the total amount of sucrose and the fatty acid methyl ester to dissolve them. They are reacted in the presence of an alkaline catalyst such as potassium carbonate (K2CO3) under reduced pressure of 20 to 30 Torrs at a temperature of 80° to 90° C. for several hours, whereby the SE is easily produced in a conversion of at least 90 % (based on the fatty acid methyl ester).

In order to deactivate the alkaline catalyst, e.g. K2CO3, included in the resulting reaction mixture, an equivalent amount of an organic acid such as lactic acid or acetic acid, or a mineral acid such as hydrochloric acid or sulfuric acid is added to the reaction mixture. By this neutralization, the catalyst changes to a corresponding salt, e.g. a potassium salt such as potassium lactate, according to the kind of the acid used in the neutralization.

The reaction solvent (e.g dimethylsulfoxide) is then distilled away under vacuum. The thus obtained residue (reaction mixture after subjected to the neutralization and vaporization of solvent) has approximately the following composition.

| Ingredients | % by weight |
| --- | --- |
| SE | 15.0 to 74 |
| Unreacted sucrose | 1.0 to 80 |
| Unreacted fatty acid methyl ester | 0.5 to 10 |
| Salt derived from $K_2CO_3$ | 0.05 to 7 |
| Soap | 1.0 to 10 |
| Fatty acid | 0.5 to 10 |
| Volatile material (remaining reaction solvent) | 3.0 to 30 |

In that case, the proportion of the monoester in the SE is from 10 to 75 % by weight and the proportion of di- and higher esters is from 90 to 25 % by weight Also, the acid radical mainly included in each of the fatty acid methyl ester, soap and fatty acid is usually a saturated acid radical having 16 to 22 carbon atoms common to them.

To the reaction mixture from which the solvent is partly distilled away and which has the above-mentioned composition, water is added in a water/reaction mixture ratio of 5 : 1 to 40 : 1 by weight, preferably 20 : 1 by weight, while the pH is adjusted to 6.2 to 8.2, preferably 7.5.

When the ratio of water to the reaction mixture is less than 5, the viscosity of the obtained aqueous solution is high and the following procedures become difficult. Also, when excess water is added to the reaction mixture such that the weight ratio of water to the reaction mixture exceeds 40, the viscosity of the obtained aqueous solution is low and accordingly the following procedures become easy and also the desired removal of reaction solvent can be made well, but a large energy cost is required in removing water upon recovery of unreacted sucrose, etc., thus the economy is impaired.

In order to prevent decomposition of the desired SE, it is preferable to adjust the aqueous solution of the reaction mixture to pH of 6.2 to 8.2. When the pH is more than 8.2, there is a possibility that SE is quantitatively hydrolyzed by an alkali. On the other hand, even in a weak acidic region of less than pH 6.2, there is a fear of acid hydrolysis of SE, for example, when it is exposed to a high temperature over 90° C.

To the thus pH-adjusted aqueous solution of the reaction mixture are added a neutral salt and sucrose, preferably with keeping at a temperature of 50° to 80° C. in order to salt out SE rapidly. In that case, it is preferable that the neutral salt to be added satisfies the following equation (1):

$$\frac{\text{Amount of neutral} + \text{Amount of salt formed}}{\text{salt to be added} + \text{from catalyst}} = \frac{\text{Amount of} + \text{Total amount} + \text{Total amount}}{\text{water} + \text{of salts} + \text{of sucrose}} \quad (1)$$

$$0.015 \text{ to } 0.12 \text{ by weight}$$

wherein the total amount of salts means the sum of the neutral salt to be added and the salt formed by neutralization of the catalyst used in the production of SE, and the total amount of sucrose means the sum of the sucrose to be added and the unreacted sucrose included originally.

Also, it is preferable to add sucrose in an amount satisfying the following equation (2):

$$\frac{\text{Amount of sucrose} + \text{Amount of}}{\text{to be added} + \text{unreacted sucrose}} = \frac{\text{Amount of} + \text{Total amount} + \text{Total amount}}{\text{water} + \text{of salts} + \text{of sucrose}} \quad (2)$$

$$0.025 \text{ to } 0.20 \text{ by weight}$$

In addition to the above equations (1) and (2), it is also preferable that the total amount of salts and the total amount of sucrose satisfy the following equation (3):

$$\frac{\text{Total amount of salts}}{\text{Total amount of sucrose}} = \frac{0.4 \text{ to } 0.6}{\text{(preferably 0.5) by weight}} \quad (3)$$

Any of neutral salts can be used so long as they are soluble in water and nontoxic. Representative examples of the neutral salt are, for instance, sodium chloride, Glauber's salt ($Na_2SO_4 \cdot 10H_2O$), potassium lactate and potassium acetate.

It has been found that when the aqueous solution containing SE precipitate obtained by adding neutral salt and sucrose so as to satisfy the equations (1), (2) and (3) is heated to a temperature of 50° to 80° C., approximately the whole amount of SE is precipitated even if the content of the volatile material (remaining reaction solvent) in the reaction mixture widely ranges from 3.0 to 30.0 % by weight, and 1 regardless of the kinds of the above-mentioned neutral salts to be added. This is a peculiar phenomenon and is of important value in connection with the objects of the present invention. By utilizing this phenomenon, SE can be separated in the form of a slurry or cake from the whole sucrose (unreacted sucrose and the sucrose added for the precipitation), the volatile material, the salt derived from the catalyst and the neutral salt which have transferred to the aqueous phase. Since the aqueous phase is not acidic, sucrose is not decomposed and, therefore, it can be recovered and reused, as occasion demands.

FIG. 1 is a triangular graph showing the above-mentioned phenomenon in more detail When Y (g) is the weight of SE dissolved in an aqueous phase and X (g) is the weight of SE precipitated, the weight percentage ($\phi$%) of SE dissolved in the aqueous phase based on the total SE (X+Y) is shown by the following equation:

$$\phi = \frac{Y}{X+Y} \times 100 \text{ (\% by weight)}$$

The change in the value $\phi$ under the following conditions is shown in the accompanying drawing.

| Conditions |  |
| --- | --- |
| Temperature = 80° C. |  |
| pH = 7.5 |  |
| Water/reaction mixture = 7.4/1 by weight |  |
| Fatty acid radical: stearic acid |  |
| Composition of reaction mixture | (% by weight) |
| SE | 29% |
| Unreacted sucrose | 35% |
| Unreacted fatty acid methyl ester | 2% |
| Salt derived from catalyst | 1% |
| Soap | 3% |
| Fatty acid | 1% |
| Volatile material (remaining reaction solvent) | 29% |
| Composition of SE | (% by weight) |
| Monoester | 73% |
| Di- and higher esters | 27% |

In the drawing, the total salt and the total sucrose are as defined above, and the sum of water, total salt and total sucrose is 100 % by weight.

The shaded part in FIG. 1 shows the region simultaneously satisfying the equations (1), (2) and (3) which has been discovered by the present inventors.

By adding the determined amounts of sucrose and neutral salt to be dissolved in the aqueous solution of the reaction mixture so as to fall within the shaded region, approximately the whole amount of SE can be precipitated, and by separating the precipitate from the aqueous phase, for example, by means of filtration or centrifugation, the volatile material (remaining reaction solvent), salt derived from catalyst, neutral salt added and the whole sucrose dissolved in the aqueous phase can be completely removed.

It is also important to selectively separate and recover only sucrose (unreacted sucrose and the sucrose added for salting cut) from the thus treated aqueous solution from which the precipitated SE has been removed, thus which contains sucrose separated with water, the salt derived from catalyst ($K_2CO_3$), the neutral salt added for salting out and the volatile material. The present inventors have found that utilization of a reverse osmosis membrane is particularly effective for this purpose. After separating the precipitated SE in a usual manner, for example, by filtration, the filtrate is subjected to reverse osmosis.

It is expected that if a fractionation molecular weight ranging from 130 to 200 is selected as that of the reverse osmosis membrane, the unreacted sucrose (molecular weight: 342) and the SE (molecular weight: more than 600) which has incidentally leaked into the aqueous phase in the prior steps such as the salting out step, would be filtered off without any problem by the reverse osmosis treatment. On the other hand, substances having a molecular weight less than the fractionation molecular weight of 130 to 200, namely the salt derived from catalyst such as potassium lactate (molecular weight: 128), the neutral salt added, and the volatile component such as dimethylsulfoxide (molecular weight: 78) would pass through fine pores of the reverse osmosis membrane without any problem.

As a result of conducting a large number of experiments on the basis of the above presumption, it has been found that when an aqueous solution containing sucrose, the salt derived from catalyst, the neutral salt added in the salting out step and the volatile material, and sometimes further a slight or trace amount of SE, is brought into contact with a reverse osmosis membrane having a fractionation molecular weight of about 150 to about 200 at a temperature of 40° to 60° C. under a pressure, the salt derived from catalyst, the neutral salt and the volatile material easily pass with water through fine pores of the membrane. By this reverse osmosis procedure, low molecular weight substances such as the salts, volatile material and water are separated from the impure aqueous sucrose solution (which may contain a slight amount of SE) to thereby form the concentrated aqueous solution of crude sucrose. An aqueous sucrose solution having a higher purity can be obtained by dissolving the concentrate in fresh water again and subjecting the solution to the reverse osmosis treatment in the same manner, and if necessary, further repeating these procedures.

The temperature of the aqueous solution to be fed to the reverse osmosis is important for obtaining a good result. If the temperature is lower than 40° C., the treating ability is remarkably lowered. Accordingly, it is desirable to select a temperature over 40° C. from a practical point of view. On the other hand, it is advisable to conduct the treatment at a temperature below 60° C., since there is a possibility that the heat resistance of the reverse osmosis is changed at a temperature over 60° C. The pH of the aqueous solution to be treated is also important, and the pH ranging from 6.2 to 8.2 is preferred because a fear of influence on the quality of sucrose is minimized.

Recently, various reverse osmosis membranes have been put on the market from various companies. Among them, for instance, reverse osmosis membranes of polyamide, crosslinked polyamide or polyether have excellent properties such as durability, heat resistance, acid resistance and alkali resistance, fungus resistance and pressure resistance. Such membranes are commercially available, for example, under a trade mark "SU-200" from Toray Engineering Kabushiki Kaisha, which has a fractionation molecular weight of about 200 and is suitable to attain the objects of the invention.

In the case of using the reverse osmosis membrane with the fractionation molecular weight of about 200, the treatment of the aqueous solution can be achieved with an industrially acceptable capacity by adjusting the upper limit of the concentration of the solute in the aqueous solution to be supplied to the membrane to about 10–20 % by weight, preferably about 15 % by weight.

When the solute concentration is more than 20 % by weight, it is difficult to pass water, the salt derived from the catalyst and the volatile material through fine pores of the membrane, and accordingly it is obliged to increase a pressure to be applied as the actuation force for reverse osmosis, thus resulting in increase of the area of the reverse osmosis membrane. This is also very uneconomical because of necessity of great electric power. On the other hand, when the aqueous solution contains the solute in a concentration of not more than about 10–15 % by weight, it is sufficiently possible to industrially isolate sucrose.

For example, when passing an aqueous solution having the composition shown in Table 1 through the reverse osmosis membrane "SU-200" with an effective area of 8 m2 per unit at 50° C. and pH 7.5 and under a pressure applied as the actuation force for reverse osmosis of 56.0 kg/cm2G, the sucrose isolation velocity of 7.3 kg/hour is achieved Other reverse osmosis membranes similar to "SU-200", commercially available from companies other than Toray Engineering Kabushiki Kaisha, also give similar results.

TABLE 1

| Components | Weight (kg) |
|---|---|
| Sucrose fatty acid ester (stearate) | 0.4 |
| Sucrose | 39.0 |
| Potassium lactate | 9.0 |
| Volatile material (reaction solvent) | 5.0 |
| Soap and fatty acid | 0.1 |
| Subtotal | 53.5 |
| Water | 481.0 |
| Total | 534.5 |

Like this, by repeating the reverse osmosis membrane treatment, the salt derived from the catalyst, the added neutral salt and the volatile material are sufficiently removed from the aqueous solution. The thus obtained aqueous solution containing sucrose can keep a sucrose concentration of about 15 to 20 % by weight. It is economically disadvantageous as well as technical difficulty to obtain the aqueous solution of sucrose with a concentration of more than 20 % by weight by the reverse osmosis means. Accordingly, when it is desired to obtain the aqueous solution of sucrose having a sucrose concentration of more than 20 % by weight, the solution is concentrated by using a usual concentration apparatus such as a multiple effect evaporator to the desirable concentration such as not less than 50 % by weight. Thus recovered sucrose can be reused to the preparation of SE as a raw material or used for other purposes.

The SE precipitated and separated in the salting out step is in the form of a slurry. It still contains a slight amount of impurities such as the volatile material, salts and sucrose. These impurities can be easily removed by treating the slurry with an acidic water.

An aqueous slurry or cake of crude SE obtained in the salting out step is washed with an aqueous solution of an acid having a pH of 3.0 to 5.5. The acid is not particularly limited. Preferable examples of the acid are, for instance, a mineral acid such as hydrochloric acid or sulfuric acid, and an organic acid such as acetic acid or lactic acid. Preferably, the acid solution is kept at a temperature of 10° to 40° C. By this treatment, the impurities such as volatile material, sucrose, neutral salt and catalyst-derived salt can be transferred into the acidic water. When the temperature of the acidic water is higher than 40° C., the viscosity rises to hinder the operation in addition to a fear of acid decomposition of SE if the operation for a long period of time, for example, over several months, is required. On the other hand, it is uneconomical to keep the acidic water at a low temperature lower than 10° C., because a cooling device is required therefor. Accordingly, the acid solution treatment is effected usually at a temperature of 10° to 40° C., preferably at ordinary temperature.

Only the above-mentioned four components included in the cake or slurry, namely volatile material (reaction solvent), sucrose, neutral salt and salt formed by neutralization of the catalyst, should be removed from the cake or slurry by the acid treatment. Accordingly, it is desirable that the SE cake or slurry is in the form of particles as small as possible so that the impurities are easily released or eluted into water upon washing with acidic water. This can be efficiently attained by conducting the washing in a device having an ability to break into small particles, for example, a mixer (such as "homomixer" made by Tokushu Kiki Kogyo Kabushiki Kisha), a homogenizer, or a colloid mill, whereby substantially the whole amounts of the above-mentioned impurities included in the SE cake or slurry can be transferred into the acidic water.

In the washing of the precipitate with an acidic water, there is observed a noticeable phenomenon that SE having a high HLB (hereinafter referred to as "high HLB-SE") included in the precipitate begins to dissolve into the acidic water. The solubility of high HLB-SE varies depending on the temperature, pH, etc. of the system. For example, when the temperature and pH of the system are ordinary temperature and 3.5, respectively, the solubility is as shown in FIG. 2.

The high HLB-SE has a high solubility in water, and here it is referred to as "water-soluble SE" and assigned with mark "Y". Since Y has a high HLB and accordingly a high water solubility, it does not precipitate even in the acidic aqueous solution and is present therein in a dissolved state. In contrast, SE having a low HLB (hereinafter referred to as "low HLB-SE") has a low water solubility, and in general it tends to deposit in an acidic water having a certain acidity. Here, the low HLB-SE is referred to as "depositable SE" and assigned with mark "X". Since X has a low HLB, it is apt to deposit from an acidic aqueous solution thereof.

Figure 2:
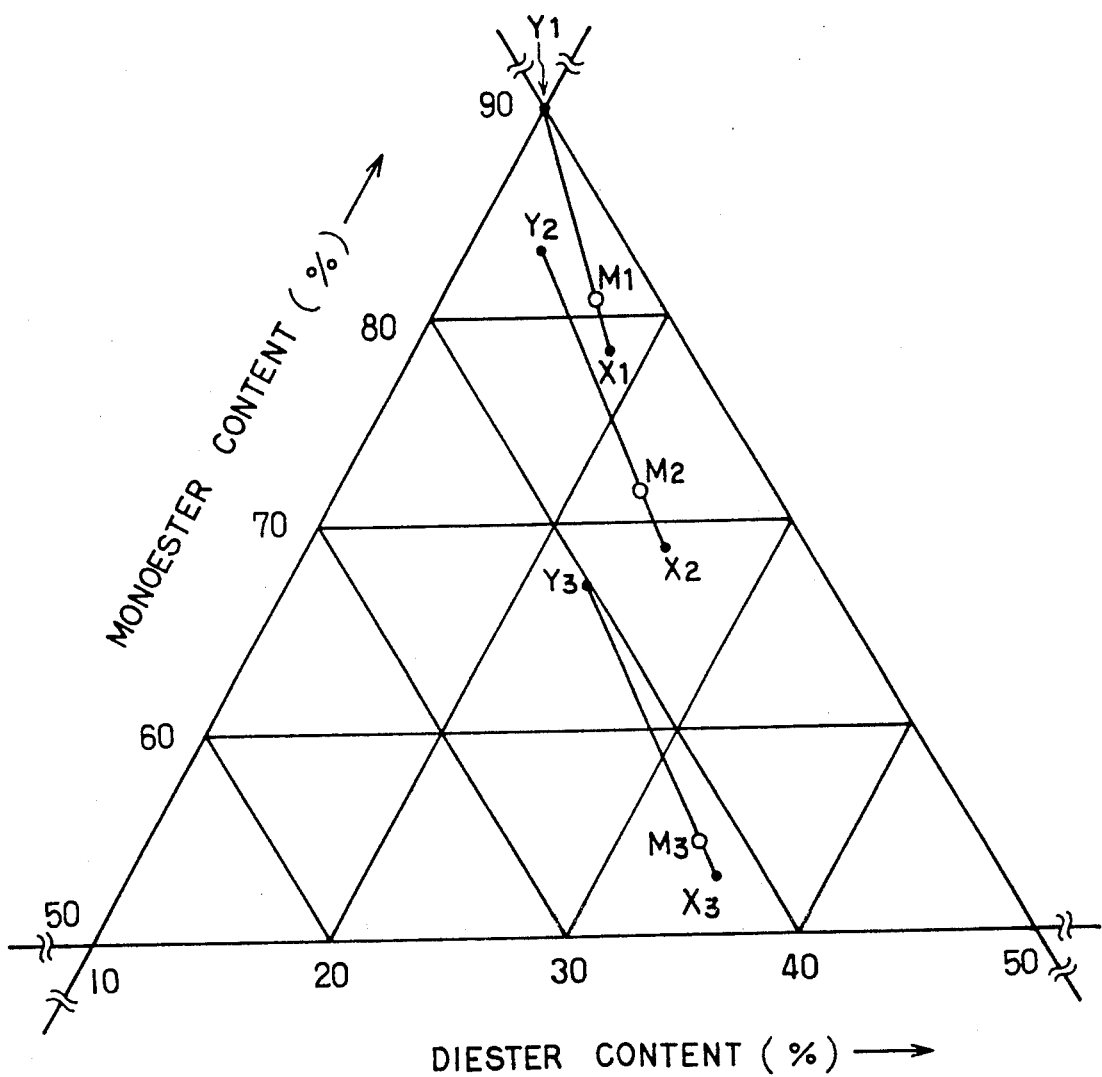

FIG. 2 shows a part of a triangular graph wherein the total of monoester, diester and triester is 100 %. In FIG. 2, point M indicates the composition of an original sample SE, point X indicates the composition of the depositable SE which has a low HLB, and point Y indicates the composition of the water-soluble SE which has a high HLB. Also, suffixes 1, 2 and 3 attached to M, X and Y show SE having a different proportions of sucrose esters (different ester distribution).

For example, in FIG. 2, when an aqueous acid solution of pH 3.5 is added to a SE sample M2 cosisting of 73 % by weight of monoester, 22 % by weight of diester and 5 % by weight of triester, the SE is divided into a dipositable SE (X2) consisting of 68 % by weight of the monoester, 25 % by weight of the diester and 7 % by weight of the triester, and the water-soluble SE (Y2) consisting of 84 % by weight of the monoester, 13 % by weight of the diester and 3 % by weight of the triester.

The weights WX2 of X2 and WY2 of Y2 divided from M2 are obtained by solving the following equations (a) and (b):

$$WM_2 = WX_2 + WY_2 \quad (a)$$

$$WY_2 \cdot \overline{Y_2M_2} = WX_2 \cdot \overline{X_2M_2} \quad (b)$$

wherein $\overline{Y_2M_2}$ is the distance between point M2 and point Y2, $\overline{X_2M_2}$ is the distance between point X2 and point M2, WM2 is the weight of M2WX2 is the weight of X2, and WY2 is the weight of Y2, provided that the weights are those of the dried matters.

Like this, SE having a relatively high monoester content (namely SE having a high HLB) is easy to dissolve into the acidic water, whereas SE having a relatively low monoester content (namely SE having a low HLB) is easy to present on the precipitate side. By utilizing this property, the SE included in the reaction mixture can be quantitatively divided into a high HLB-SE and a low HLB-SE. There has also been found a tendency that in general, the higher the monoester content in SE, the more increased the amount of SE (Y) dissolved in water be, and in the reverse case, the amount of SE (Y) dissolved in water is decreased. With respect to how much SE having a certain composition is dissolved in an acidic water, it can be quantitatively determined by substituting the data φ shown in FIG. 1 in the equations (a) and (b) to give the values WX and WY.

Since the aqueous acid solution obtained in the washing step contains a relatively large amount of high HLB-SE, it is separated from the precipitated SE composed mainly of low HLB-SE in a usual manner such as filtration or centrifugation. The obtained filtrate or supernatant contains, in addition to the high HLB-SE, small amounts of the volatile material (such as dimethylsulfoxide), salts and sucrose and, therefore, it is necessary to further purify the SE.

By many experiments we have found that ultrafiltration is suitable for removing these impurities from high HLB-SE in the filtrate or supernatant It is known that sucrose fatty acid ester molecules aggregate with each other to form high molecular weight micelles under certain conditions in the aqueous solution.

Sucrose monoester, diester and triester are compounds wherein 1, 2 or 3 fatty acid residues are attached to any of oxygen atoms of the 3 primary hydroxyl groups of sucrose molecule, respectively. As well known, since the monoester is low in ability to form micelles in water while having a larger hydrophilic property than diester and triester, it forms a relatively low weight micelle (in other words, a micelle having a small diameter). In contrast, the diester and triester have a very large micelle forming ability while being relatively low in hydrophilic property and, therefore, they form micelles of very large weight (namely large micellar diameter). It is seldom that the sucrose fatty acid ester is produced and put on the market in the form of monoester alone. Commerially available sucrose fatty acid esters are usually those produced in the form of a mixture having a monoester content of 70 %, 50 %, 30 % or the like.

According to the investigation of the present inventors, since high HLB-SE having a high monoester content, for instance, as high as 70 %, forms micelles of a lower weight in comparison to low HLB-SE having a monoester content as low as 50 %, the microscopic diameter of micelle is small as much and it has a tendency to pass through a ultrafiltration membrane having a specified pore diameter in comparison with low HLB-SE having a monoester content of 50 %. Therefore, high HLB-SE having a high monoester content has an undesirable tendency to pass through the membrane together with the unreacted sucrose, a salt formed by neutralization of a reaction catalyst with an acid, and a volatile material. Such a problem can be easily eliminated by selecting the ultrafiltration membrane, and it is necessary for recovery of high HLB-SE to select the membrane having a low fractionation molecular weight (namely small pore diameter) when desired to remove sucrose, salts and volatile material from high HLB-SE having a high monoester content, and it is necessary for recovery of low HLB-SE having a low monoester content to select the membrane having a large fractionation molecular weight (namely large pore diameter).

It is confirmed by the present inventors that it is practically impossible to separate the unreacted fatty acid ester such as fatty acid methyl ester, soap and fatty acid among substances included in the reaction mixture from SE by a filtration means because they are present in the state of being included in the micelles of SE. In other words, impurities permeable together with water to a filtration membrane having an appropriate fractionation molecular weight by a given pressure as actuating force are the sucrose (unreacted sucrose and sucrose for salt out), a salt derived from the catalyst, a neutral salt added and a volatile material (polar materials having a high affinity for sucrose and a high affinity for fatty acid ester which have been used as reaction solvents in synthesis of SE, e.g. dimethylsulfoxide and dimethylformamide), while the unreacted fatty acid ester, soap and free fatty acid are entrapped in the sucrose ester micelles and they are not impermeable to the filtration membrane.

Thus, in this ultrafiltration step, by skillfully utilizing these facts and by selecting a filtration membrane having an appropriate fractionation molecular weight, the sucrose, salts and volatile material are removed together with water from other components, namely SE, unreacted fatty acid ester, soap and fatty acid.

In order to select a ultrafiltration membrane having an adequate fractionating molecular weight, it is necessary to previously know approximate molecular weights of the subject substances. The molecular weights of typical single compounds involved in the present invention are defined approximately as follows:
(1) Sucrose = 342
(2) Unreacted fatty acid methyl ester
   (main) Methyl stearate = 290
(3) Salt produced by neutralization of catalyst ($K_2CO_3$)
   In case of lactic acid: potassium lactate = 128
   In caser of acetic acid: potassium acetate = 98
(4) Volatile material
   Dimethylsulfoxide = 78
   Dimethylformamide = 73
(5) Sucrose fatty acid ester (single compound not forming micelle)
   (main) Sucrose monostearate = 600
   (main) Sucrose distearate = 858
   (main) Sucrose tristearate = 1116
Other sucrose fatty acid esters such as myristate, palmitate, arachate and behenate have also similar molecualr weights to the above molecular weights.
(6) Soap
   (main) Sodium stearate = 298
   (main) Potassium stearate = 314
(7) Fatty acid
   (main) Stearic acid = 276
(8) Water = 18

On the supposition that the apparent molecular weight of a sucrose fatty acid ester micelle may be approximately estimated as follows, if 10 molecules associate per micelle, the apparent molecular weight of the micelle is:
molecular weight of monoester (600) × 10 = 6,000 (regarded as 100 % monoester),
molecular weight of diester (858) × 10 = 8,580 (regarded as 100 % diester), and
molecular weight of triester (1,116) × 10 = 11,160 (regarded as 100 % triester).
Since the actual SE is a mixture composed mainly of mono-, di- and triesters, the apparent molecular weight of a SE micelle is defined as the average value thereof. The selection of a membrane for ultrafiltration adequate for the purposes of the present invention is conducted as follows:

In case of a ultrafiltration membrane having a fractionating melecular weight of 200, even if it is attempted to remove the unreacted sucrose, the salts such as $K_2CO_3$ and the volatile material (organic solvent) while feeding the washing liquid obtained in the previous step with applying a pressure, the components separable by such a membrane are only water, the salts and the organic solvent which have lower molecular weights than the fractionating molecular weight 200 of the membrane. Since sucrose which has a molecular weight of 342 larger than the fractionating molecular weight 200, is impermeable to the membrane, it cannot be separated and removed from SE.

In case of a ultrafiltration membrane having a fractionating molecular weight of 5,000, sucrose, salts and volatile material can easily pass throught fine pores of the membrane, since they have a molecular weight less than 5,000. SE forms micelles as mentioned above, and accordingly it is estimated to have an apparent molecular weight of 6,000 or more on the assumption that the number of sucrose ester molecules associated may be 10 or more. Therefore, the micelles would not be permeable to the membrane having a fractionating molecular weight of 5,000. Since the apparent molecular weight of the micelle would be in fact more than 6,000, a membrane having a fractionating molecular weight of more than 5,000 can be used and this is experimentally confirmed by the present inventors.

Investigation has been made also with respect to a membrane having a fractionating molecular weight of 1,000. The results are as expected, and such a membrane can be used in the present invention.

The ultrafiltration membrane is selected from those having a fractionation molecular weight of 1,000 or more in view of the size or weight of micelles of the sucrose fatty acid esters, treatment efficiency and other conditions. According to the present invention, by suitably selecting the fractionation molecular weight of the ultrafiltration membrane, it is possible to efficiently remove impurities including sucrose.

The ultrafiltration membrane should also satisfy the following conditions.
(1) It has a resistance to a physical external force.
(2) It has a thermal resistance, and is not decomposed by microorganisms.
(3) It has an appropriate fractionating molecular weight and has a large treating ability.
(4) The working life is long.
(5) It is available with an economical cost.

The advance of technique of the preparation of ultrafiltration membrane in recent years is marked, and therefore the membranes satisfying the above conditions are available also from those put on the market.

The washing liquid, namely an aqueous solution containing a water-soluble high HLB-SE (Y), obtained in the prior step, is neutralized with an alkali prior to conducting the ultrafiltration to adjust to a pH of 6.2 to 8.2, preferably a pH in the vicinity of 7.5 in order to prevent the hydrolysis of SE. When the pH is more than 8.2, the hydrolysis of SE is easy to occur. When the pH is less than 6.2, micelles of the SE are hard to be formed, thus resulting in loss of SE due to passing through filtration membrane, or resulting in choking of pores of the membrane.

The thus neutralized aqueous solution is kept at a temperature of not higher than 80° C. during the ultrafiltration regardless of the kind of the fatty acid methyl ester. When the temperature of the aqueous solution exceeds 80° C., SE may be decomposed. In particular, the highest filtration velocity is obtained when the temperature of the aqueous solution to be filtered falls within the range of 40° to 60° C. That is to say, sucrose, salt derived from the catalyst such as K2CO3, neutral salt added and volatile material such as dimethylsulfoxide or dimethylformamide pass the most efficiently through the filtration membrane with water, when the filtration temperature is kept at 40° to 60° C., especially in the vicinity of 50° C. The reason is considered that as a result that SE forms huge micelles at a temperature of 40° to 60° C., the total number of micelles decreases and substances which do not take part in micelle formation, such as sucrose, become hard to subject to a resistance of SE, thus these substances become easy to move and pass through the membrane.

The SE-containing aqueous solution maintained at a temperature of 40° to 60° C. is brought into contact with a ultrafiltration membrane at a hydrogen ion concentration corresponding to a pH of 6.2 to 8.2 under a pressure of 1 to 20 kg/cm2G applied as actuation source for ultrafiltration by a pump.

As stated before, it is important to determine the fractionation molecular weight of filtration membrane so that the impurities can be separated efficiently without leakage of SE at a high filtration velocity The present inventors have found that membranes having a fractionation molecular weight of 1,000 to 100,000 are suitable for the purposes of the present invention, whereby the purification can be carried out without impairing the separability of sucrose, salts and volatile material at a high filtration velocity, and particularly membranes having a fractionation molecular weight of about 5,000 is the most suitable for the treatment on an industrial scale. The filtration velocity decreases with decreasing the fractionation molecular weight. On the other hand, when the fractionation molecular weight is high, namely within a range exceeding 5,000 and up to 100,000, the sucrose ester may leak. However, such a leakage is slight even if occurs, and is not economically detrimental.

Cellulose membranes are not much preferred in practical use, since they are weak against a physical force and are easily attacked with microorganisms. Polysulfone and polyvinylidene fluoride membranes reinforced by a support layer are suitable in practical use, and these filtration membranes are commercially available. They have excellent thermal, acid and alkali resistances and can withstand a physical external force, and moreover microorganisms do not propagate on the membrane surface. Representative examples of commercially available ultrafiltration membranes suitable for the process of the present invention are, for instance, polyvinylidene fluoride membrane (trade mark "TERP-E-5") and polysulfone membranes (trade mark "TERP-HF-10" and "TERP-HF-100") which are sold by Toray Engineering Kabushiki Kaisha.

By the ultrafiltration treatment, impurities such as volatile material, sucrose and salts are removed from the washing liquid obtained in the prior step of washing the precipitate with acidic water, thus a high HLB-SE (Y) having a high purity is recovered usually with the concentration of a 5 to 15 % by weight aqueous solution. The thus purified SE contains the monoesters in a high proportion. For example, in case of the crude SE (M2) having a monoester content of 73 % by weight shown in FIG. 2, it is divided into a high HLB-SE having a monoester content of 84 % by weight and a low HLB-SE having a monoester content of 68 % by weight. Such a high HLB-SE has hitherto not been prepared easily.

The thus obtained aqueous solution of high HLB-SE can be concentrated up to about 25 % by weight in a usual manner under vacuum, but the solution form is inconvenient for handling, transportation or the like. Preferably, the high HLB-SE should be in the form of a powder. Spray drying is optimum for the dehydration of the aqueous SE solution, and has many advantages as compared with other drying methods. As mentioned before, in case of using a usual vacuum dryer as represented by a so-called agitated vacuum dryer, or a flash dryer, deterioration of the quality such as rise in acid value of SE product, coloration or caramel formation is unavoidable due to peculiar viscosity characteristic and low softening or melting point of SE, and in the latter case, a risk of dust explosion cannot be disregarded, too. The spray drying according to the present invention can solve these problems.

In the present invention, the aqueous SE solution is continuously fed to a spray drying tower by a pump, dispersed in the form of mist through a nozzle or by a centrifugal force of a rotary disk, and brought into contact with a dry air stream. Since the surface area of water evaporation is made extremely large by spray drying, dehydration and drying can be completed in a very short time, e.g. in several seconds after spraying. The rotary disc type dryer is preferred from the viewpoint of a high viscosity of the solution.

The SE solution fed to the spray drying tower whose concentration is 4 to 40 % by weight is kept at a temperature of 40° to 80° C., preferably 40° to 60° C. in consideration of quality. In case of spraying the solution by means of a rotary disk, the number of rotations thereof is from 15,000 to 24,000 r.p.m. when the diameter of the disk is from 5 to 10 cm.

The air passed through the tower should have a heat energy sufficient to evaporate water in the solution, and accordingly when the temperature of the air is low, a large quantity of air is required as a matter of course. The temperature of the air can be selected from a range of 10° to 100° C., but in consideration of drying efficiency and prevention of thermal decomposition of the sucrose ester product, the temperature of the air is preferably selected from a range of 60° to 80° C.

The humidity of the air passed is also important as well as the temperature, and it is economical that the absolute humidity of the air is from 0.008 to 0.05 kg water/kg dry air, especially from 0.01 to 0.04 kg water/kg dry air.

The parameters such as volume, diameter and height of the spray drying tower are determined on the basis of the above-mentioned spraying conditions. Under appropriate conditions, powder of high HLB-SE having a water content of not more than 5 % by weight can be continuously taken out from the lower part of the tower. The obtained dry product is very excellent in quality, e.g. color and stench because of short heat time, and also this drying work does not require many hands.

In general, the thus obtained powder contains 0.5 to 5.0 % by weight of water, 0.5 to 10.0 % by weight of unreacted fatty acid methyl ester, 0.5 to 10.0 % by weight of a soap, 0.5 to 10.0 % by weight of a fatty acid and 98.0 to 80.0 % by weight of high HLB-SE.

Like this, according to the purification technique using water of the present invention, the volatile material (reaction solvent) remaining in the reaction mixture containing SE produced by a reaction of sucrose and a fatty acid alkyl ester can be easily removed without using an organic solvent as a purification solvent, while sucrose can be easily recovered in a high purity. Further, from the crude SE from which the volatile material and sucrose have been removed, an aqueous solution of purified high HLB-SE can be easily obtained by washing the crude SE with an acidic water and then subjecting the washing liquid to ultrafiltration. When the concentrate obtained in the ultrafiltration is further spray-dried, a dry powder of highly pure high HLB-SE having a good flowability can be easily, continuously obtained without imparing the quality, e.g. color and stench.

The present invention is more specifically described and explained by means of the following Examples in which all % are by weight unless otherwise noted. It is to be understood that the present invention is not limited to these Examples.

EXAMPLE 1

A reaction solvent was distilled away in a usual manner from a reaction mixture formed by a reaction of sucrose and methyl stearate according to the solvent method, and it was neutralized with lactic acid to give a residue having the composition shown in Table 2.

TABLE 2

| Ingredients | Amount % | kg |
|---|---|---|
| SE (stearate)* | 35.2 | 35.2 |
| Unreacted sucrose | 37.5 | 37.5 |
| Unreacted fatty acid methyl ester (methyl stearate) | 1.5 | 1.5 |
| Potassium lactate | 1.2 | 1.2 |
| Soap | 2.1 | 2.1 |
| Stearic acid | 1.3 | 1.3 |
| Dimethylsulfoxide (DMSO) (reaction solvent) | 21.2 | 21.2 |
| Total | 100.0 | 100.0 |

(Note):
*SE had a monoester content of 70% and a di- or higher-ester content of 30%.

After drying the residue, to 100 kg of the dried matter was added 1,000 kg of water to dissolve it.

To the obtained aqueous solution were added 62.5 kg of sucrose and 97.6 kg of a 50 % aqueous solution of potassium lactate and the temperature was elevated to 75° C. The resulting precipitate was filtered off to give a cake (water content: 45 %), and it was dried at 80° C. in a vacuum. The composition of the dried cake is shown in Table 3.

TABLE 3

| Ingredients | Amount % | kg |
|---|---|---|
| SE | 79.5 | 35.0 |
| Unreacted fatty acid methyl ester | 3.4 | 1.5 |
| Soap | 4.8 | 2.1 |
| Fatty acid | 3.0 | 1.3 |
| Dimethylsulfoxide | 2.5 | 1.1 |
| Sucrose | 5.8 | 2.5 |
| Others | 1.0 | 0.5 |
| Total | 100.0 | 44.0 |

Measurement of the filtrate (1,180 kg) according to gel permeation chromatography (GPC) indicated that there was no SE in the filtrate and that 95 % of dimethylsulfoxide as the reaction solvent was removed.

In 400 kg of an aqueous solution of acetic acid (pH 3.5) having room temperature was dispersed 80 kg of the thus obtained cake. The dispersion was stirred in a homomixer for 10 minutes to wash and uniformly break the precipitate into small particles, and was then filtered. This washing operation was repeated four times in total. The composition of the obtained filtrate (pH 3.5) is shown in Table 4.

TABLE 4

| Ingredients | Amount % | kg |
|---|---|---|
| SE | 66.1 | 7.8 |
| Unreacted fatty acid methyl ester | 1.7 | 0.2 |
| Fatty acid | 4.2 | 0.5 |
| DMSO | 8.5 | 1.0 |
| Sucrose and others | 19.5 | 2.3 |
| Subtotal | 100.0 | 11.8 |
| Water | 0.0 | 1,613.2 |
| Total | 100.0 | 1,625.0 |

After adjusting 1,625 kg of the filtrate to pH 7.5 with sodium hydroxide, it was fed to a spiral type 4 inch cylindrical pressure filtration unit of membrane area 8 m2 equipped with a ultrafiltration membrane having a fractionation molecular weight of 5,000 (commercially available under the trade mark "TERP-E-5" from Toray Engineering Kabushiki Kaisha) under the following conditions.

Pressure: 7.5 to 9.2 kg/cm2G
Temperature: 50.5° to 53.0° C.
Discharge velocity of filtrate: 4.1 to 5.7 kg/8 m2.min.
Circulation velocity inside the membrane: 18.9 to 17.3 kg/8 m2.min.

After about 310 minutes from the start of feeding, to the concentrate which had not passed through the ultrafiltration membrane was added 1,600 kg of water, and it was stirred for dissolution and fed to the above cylindrical pressure filtration unit again under the same conditions. This filtration operation was repeated four times in total. The obtained concentrate had a composition (as the dried matter) shown in Table 5 and a solid content of 11.5 %.

TABLE 5

| Ingredients | Amount % | kg |
|---|---|---|
| SE | 91.6 | 7.7 |
| Unreacted fatty acid methyl ester | 2.4 | 0.2 |
| Fatty acid | 6.0 | 0.5 |
| DMSO | (1.1 ppm) | — |
| Sucrose and others | 0.0 | 0.0 |
| Total | 100.0 | 8.4 |

The concentrate having the composition shown in Table 5 was adjusted to pH 7.5. The thus pH-adjusted concentrate (aqueous solution) had a composition (as the solid matter) shown in Table 6.

TABLE 6

| Ingredients | Amount % | kg |
|---|---|---|
| SE* | 91.6 | 7.7 |
| Unreacted fatty acid methyl ester | 2.4 | 0.2 |
| Soap | 4.1 | 0.34 |
| Fatty acid | 1.9 | 0.16 |
| DMSO | (1.1 ppm) | — |
| Total | 100.0 | 8.4 |

(Note)
*SE had a monoester content of 83.2% and a di- or higher-ester content of 16.8%.

The pH-adjusted solution was heated in a vaccum to concentrate. The obtained concentrate contained 24 % of a high HLB-SE having a monoester content of about 83 %.

On the other hand, the solid residue obtained by washing the cake having the composition shown in Table 3 with acetic acid contained SE having a monoester content of 67 %, namely was a low HLB-SE.

EXAMPLE 2

The procedure of Example 1 was repeated to give the concentrate having the composition (as solid matter) shown in Table 6 and containing 24 % of a high HLB-SE having a monoester content of about 83 %.

The obtained concentrate was fed into a spray drying tower under the following conditions.
Diameter of spray drying tower: 2.0 m
Length of true cylindrical portion: 1.5 m
Fed air: 350 N m3/hour
Diameter of rotary disk: 10 cm
Number of rotations of the disk: 24,000 r.p.m.
Temperature of air at inlet: 51° C.
Absolute humidity of air at inlet: 0.020 kg water/kg dry air
Feeding velocity of concentrate: 1.1 kg/hour The powdery high HLB-SE obtained from the lower part of the spray drying tower had a water content of 2.10 %, a bulk specific gravity of 0.41, no coloration due to heating and a good flowability. The composition of the obtained powder is shown in Table 7. The drying was continued stably for 1.5 hours.

TABLE 7

| Ingredients | Amount (%) |
| --- | --- |
| SE* | 91.6 |
| Unreacted fatty acid methyl ester | 2.4 |
| Soap | 4.2 |
| Fatty acid | 1.8 |
| DMSO | (1.0 ppm) |
| Sucrose | 0.0 |
| Total | 100.0 |

(Note)
*SE had a monoester content of 83.1% and a di- or higher-ester content of 16.9%.

As shown above, from the SE having the monoester content of 70 % (di- or higher-ester content: 30 %) in the original reaction mixture, the high HLB-SE having the monoester content of 83.1 % could be obtained. The SE left as the solid in washing of the cake shown in Table 3 with acetic acid was low HLB-SE having a monoester content of 67 % as mentioned above. This fact indicates that the SE in the original reaction mixture could be fractionated into the high HLB-SE and the low HLB-SE.

EXAMPLE 3

An aqueous solution of the dried residue having the composition shown in Table 2 was prepared, salted out and filtered in the same manner as in Example 1 to give the cake of precipitate and the filtrate.

While the obtained cake having the composition shown in Table 3 was treated by washing with acidic water, ultrafiltration and spray-drying in the same manner as in Examples 1 and 2 to give a powder of high HLB-SE having the composition shown in Table 7, the above filtrate was treated in order to recover sucrose as follows:

Water was added to 1,180 kg of the filtrate (aqueous solution containing sucrose, salts and volatile material, obtained by removing SE precipitated by the above-mentioned salting-out) to give an aqueous solution having the composition shown in Table 8.

TABLE 8

| Ingredients | Amount | |
| --- | --- | --- |
|  | % | kg |
| SE | 0.01 | 0.2 |
| Sucrose | 5.83 | 97.5 |
| Potassium lactate | 2.96 | 49.5 |
| DMSO | 1.20 | 20.1 |
| Subtotal | 10.00 | 167.3 |
| Water | 90.00 | 1505.7 |
| Total | 100.00 | 1673.0 |

The aqueous solution (pH 7.4) was heated at a temperature of 50° to 52.5° C., and was fed to a reverse osmosis membrane "SU-200"(Toray's trade mark) having a diameter of 4 inches, a length of 1 m and a filtrating area of 8 m2 at a pump pressure of 58.2 kg/cm2G under the following operation conditions.
Discharge velocity of the aqueous solution passed through the reverse osmosis membrane: 3.9 to 2.2 l/minute
Circulation velocity inside the membrane: 19.2 to 20.9 l/minute
Feeding time: about 550 minutes The concentrate which had not passed through the membrane contained sucrose, the salt derived from the catalyst and the volatile material in amounts of almost whole, 46.0 % and 52.0 % of those included in the original reaction mixture, respectively. The composition of the concentrate is shown in Table 9.

On the other hand, the aqueous solution which had passed through the membrane, namely the filtrate, as shown in Table 9, scarcely contained sucrose, and contained the salt derived from the catalyst, the neutral salt and the volatile material in amounts of 54.0 % and 48.0 % of those included in the original solution to be treated, respectively.

TABLE 9

| Ingredients | Filtrate | | Concentrate | |
| --- | --- | --- | --- | --- |
|  | kg | % | kg | % |
| SE | 0.0 | 0.0 | 0.2 | 0.2 |
| Sucrose | 0.0 | 0.0 | 97.5 | 74.4 |
| Potassium lactate | 26.7 | 73.5 | 22.8 | 17.4 |
| DMSO | 9.6 | 26.5 | 10.5 | 8.0 |
| Subtotal | 36.3 | 100.0 | 131.0 | 100.0 |
| Water | 588.7 | | 917.0 | |
| Total | 625.0 | | 1048.0 | |

EXAMPLE 4

To 1,048 kg of the concentrate (solute concentration: 12.5 %) having the composition shown in Table 9, obtained in Example 3 was added 1,900 kg of water, and the thus obtained aqueous solution was fed to the reverse osmosis membrane under the same conditions as in Example 3 to isolate sucrose.

The results are shown in Table 10.

TABLE 10

| Ingredients | Filtrate | | Concentrate | |
| --- | --- | --- | --- | --- |
|  | kg | % | kg | % |
| SE | 0.0 | 0.0 | 0.2 | 0.02 |
| Sucrose | 0.0 | 0.0 | 97.5 | 96.13 |
| Potassium lactate | 15.7 | 68.2 | 7.1 | 0.70 |
| DMSO | 7.3 | 31.8 | 3.2 | 3.15 |
| Subtotal | 23.0 | 100.0 | 108.0 | 100.00 |

TABLE 10-continued

| Ingredients | Filtrate | | Concentrate | |
|---|---|---|---|---|
| | kg | % | kg | % |
| Water | 1909.8 | | 907.2 | |
| Total | 1932.8 | | 1015.2 | |

EXAMPLE 5

To 1,015.2 kg of the concentrate (solute concentrate: 10.6 %) shown in Table 10, obtained in Example 4 was added 2,000 kg of water and the thus obtained aqueous solution was fed into the reverse osmosis membrane under the same conditions as in Example 3 to isolate sucrose. The results are shown in Table 11.

TABLE 11

| Ingredients | Filtrate | | Concentrate | |
|---|---|---|---|---|
| | kg | % | kg | % |
| SE | 0.0 | 0.0 | 0.1 | 0.1 |
| Sucrose | 0.0 | 0.0 | 97.4 | 97.0 |
| Potassium lactate | 5.3 | 71.6 | 1.8 | 1.8 |
| DMSO | 2.1 | 28.4 | 1.1 | 1.1 |
| Subtotal | 7.4 | 100.0 | 100.4 | 100.0 |
| Water | 2197.4 | | 910.0 | |
| Total | 2204.8 | | 1010.4 | |

In addition to the ingredients used in the Examples, other ingredients can be used in the Examples as set forth in the specification to obtain substantially the same results.

What we claim is:

1. A process for purifying sucrose fatty acid esters having a high hydrophilic-lipophilic balance included in a reaction mixture formed by a reaction of sucrose and a fatty acid alkyl ester in an organic solvent, said reaction mixture containing sucrose fatty acid esters, unreacted sucrose, unreacted fatty acid alkyl ester, a reaction catalyst, a soap, a fatty acid and the organic solvent as a volatile material, which comprises adjusting the reaction mixture to a neutral pH region, adding water, a neutral salt and sucrose to the reaction mixture to precipitate the sucrose fatty acid esters, separating the resulting precipitate from the liquid phase, washing it with an acidic water, neutralizing the washing liquid and subjecting it to ultrafiltration.

2. The process of claim 1, wherein said reaction mixture to be treated consists essentially of 15.0 to 95.0 % by weight of sucrose fatty acid esters, 1.0 to 80.0 % by weight of unreacted sucrose, 0.5 to 10.0 % by weight of unreacted fatty acid methyl ester, 0.05 to 7.0 % by weight of a catalyst, 1.0 to 10.0 % by weight of a soap, 0.5 to 10.0 % by weight of a fatty acid and 3.0 to 30.0 % by weight of a remaining reaction solvent.

3. The process of claim 1, wherein said neutral pH region is from pH 6.2 to pH 8.2.

4. The process of claim 1, wherein after the addition of water, neutral salt and sucrose, the reaction mixture is heated to a temperature of 50° to 80° C.

5. The process of claim 1, wherein said water is added to the reaction mixture in a water/reaction mixture ratio of 5 : 1 to 40 : 1 by weight.

6. The process of claim 1, wherein said neutral salt and sucrose are added to the reaction mixture in amounts satisfying the following questions:

$$\frac{TSa}{TH_2O + TSa + TSu} = 0.015 \text{ to } 0.12$$

$$\frac{TSu}{TH_2O + TSa + TSu} = 0.025 \text{ to } 0.20$$

$$\frac{TSa}{TSu} = 0.4 \text{ to } 0.6$$

wherein TSa means the sum of the neutral salt to be added and a salt formed by neutralization of catalyst used in the synthesis of sucrose fatty acid ester, TSu means the sum of sucrose to be added and the unreacted sucrose present from the beginnng, and TH2O means the amount of water present.

7. The process of claim 1, wherein the pH adjustment of the reaction mixture is made with an acid selected from the group consisting of lactic acid, acetic acid, hydrochloric acid and sulfuric acid.

8. The process of claim 1, wherein the fatty acid radical included in each of the fatty acid alkyl ester, soap and fatty acid is a saturated fatty acid radical having 16 to 22 carbon atoms.

9. The process of claim 1, wherein said volatile material is dimethylsulfoxide or dimethylformamide.

10. The process of claim 1, wherein said neutral salt to be added to the reaction mixture is a salt selected from the group consisting of sodium chloride, Glauber's salt, potassium lactate and potassium acetate.

11. The process of claim 1, wherein said sucrose fatty acid ester is composed of 10 to 75 % by weight of the monoester and 90 to 25 % by weight of the di- and higher esters.

12. The process of claim 1, wherein said acidic water has a pH of 3.0 to 5.5.

13. The process of claim 1, wherein the water is maintained at a temperature of 10° to 40° C.

14. The process of claim 1, wherein the membrane used for the ultrafiltration is made of a polysulfone or a polyvinylidene fluoride.

15. The process of claim 1, wherein the membrane for the ultrafiltration has a fractionation molecular weight of 1,000 to 100,000.

16. The process of claim 1, wherein said ultrafiltration is carried out under a pressure of 1.0 tp 20.0 kg/cm2G.

17. The process of claim 1, wherein the washing liquid is neutralized to pH 6.2 to 8.2.

18. The process of claim 1, wherein the washing liquid subjected to ultrafiltration is maintained at a temperature of 40° to 60° C.

19. The process of claim 1, wherein the liquid phase obtained by separating the precipitate is subjected to reverse osmosis, thereby recovering sucrose.

20. The process of claim 19, wherein a membrane used for the reverse osmosis has a fractionation molecular weight of 150 to 200.

21. The process of claim 19, wherein said liquid phase is maintained at a temperature of 40° to 60° C. and at a pH of 6.2 8.2.

22. The process of claim 19, wherein said liquid phase has a sucrose content of 10 to 20 % by weight.

23. The process of claim 1, wherein the concentrate obtained by the ultrafiltration is spray-dried.

24. The process of claim 23, wherein said concentrate has a solid content of 4 to 40 % by weight.

25. The process of claim 24, wherein said spray-drying is conducted in an air stream having an absolute humidity of 0.008 to 0.05 kg water/kg dry air and a temperature of 10° to 100° C.

* * * * *